United States Patent
Noble et al.

(10) Patent No.: US 11,759,147 B2
(45) Date of Patent: Sep. 19, 2023

(54) SYSTEMS AND METHODS FOR REAL-TIME CONCUSSION DIAGNOSIS BY ELECTROENCEPHALOGRAM ACTIVITY MONITORING

(71) Applicant: THE TRUSTEES OF COLUMBIA UNIVERSITY IN THE CITY OF NEW YORK, New York, NY (US)

(72) Inventors: James M. Noble, Demarest, NJ (US); Barclay Morrison, New York, NY (US); Catherine Schevon, New York, NY (US); Ioannis Kymissis, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1215 days.

(21) Appl. No.: 16/307,618

(22) PCT Filed: Jun. 8, 2017

(86) PCT No.: PCT/US2017/036489
§ 371 (c)(1),
(2) Date: Dec. 6, 2018

(87) PCT Pub. No.: WO2017/214356
PCT Pub. Date: Dec. 14, 2017

(65) Prior Publication Data
US 2019/0298262 A1    Oct. 3, 2019

Related U.S. Application Data

(60) Provisional application No. 62/347,184, filed on Jun. 8, 2016.

(51) Int. Cl.
*A61B 5/00* (2006.01)
*A42B 3/04* (2006.01)
(Continued)

(52) U.S. Cl.
CPC ............ *A61B 5/6803* (2013.01); *A42B 3/046* (2013.01); *A61B 5/00* (2013.01); *A61B 5/067* (2013.01);
(Continued)

(58) Field of Classification Search
CPC ......... A61B 5/6803; A61B 5/291; A61B 5/24; A61B 5/00; A61B 5/067;
(Continued)

(56) References Cited

U.S. PATENT DOCUMENTS 3,993,046 A * 11/1976 Fernandez ........... A61B 5/7405
600/545
4,085,739 A    4/1978 Sams
(Continued)

FOREIGN PATENT DOCUMENTS

WO    WO 2009/069134 A2    6/2009
WO    WO 2014/062738 A1    4/2014

OTHER PUBLICATIONS

Foundations of Sport-Related Brain Injuries; 2006; Chapter 3: Electroencephalography and Mild Traumatic Brain Injury Robert W. Thatcher; pp. 241-265 (Year: 2006).*
(Continued)

*Primary Examiner* — Patrick Fernandes
(74) *Attorney, Agent, or Firm* — Baker Botts, L.L.P.

(57) ABSTRACT

Systems and methods for detecting concussions in real-time are provided. An exemplary system of detecting concussions in real time includes an accelerometer to measure acceleration event and generate an accelerometry signal. The system includes a plurality of electrodes to detect an electroencephalogram (EEG) and each of the electrodes can be attached to a top region of the headgear through a flexible shaft. The system further includes a signal processing circuit
(Continued)

to amplify, filter and broadcast an electroencephalogram (EEG) signal to a local wireless receiving unit.

24 Claims, 9 Drawing Sheets

(51) Int. Cl.
    *A63B 71/10*       (2006.01)
    *A61B 5/06*        (2006.01)
    *A61B 5/24*        (2021.01)
    *A61B 5/291*      (2021.01)

(52) U.S. Cl.
    CPC ............. *A61B 5/24* (2021.01); *A61B 5/291* (2021.01); *A63B 71/10* (2013.01); *A61B 2562/0215* (2017.08); *A63B 2220/40* (2013.01); *A63B 2230/10* (2013.01); *A63B 2243/007* (2013.01)

(58) Field of Classification Search
    CPC . A61B 2562/0215; A61B 5/7275; A61B 5/30; A61B 5/7405; A61B 5/316; A42B 3/046; A63B 71/10; A63B 2220/40; A63B 2230/10; A63B 2243/007; G16H 50/70; A61N 2/006
    See application file for complete search history.

(56) References Cited

U.S. PATENT DOCUMENTS

| | | | |
|---|---|---|---|
| 4,323,076 A | 4/1982 | Sams | |
| 4,913,160 A | 4/1990 | John | |
| 4,967,038 A | 10/1990 | Gevins et al. | |
| 5,083,571 A | 1/1992 | Prichep | |
| 5,230,346 A | 7/1993 | Leuchter et al. | |
| 5,539,935 A | 7/1996 | Rush, III | |
| 5,621,922 A | 4/1997 | Rush, III | |
| 5,978,972 A | 11/1999 | Stewart et al. | |
| 6,985,769 B2 | 1/2006 | Jordan | |
| 7,471,978 B2 | 12/2008 | John et al. | |
| 7,509,835 B2 | 3/2009 | Beck | |
| 7,526,389 B2 | 4/2009 | Greenwald et al. | |
| 7,904,144 B2 | 3/2011 | Causevic et al. | |
| 8,364,255 B2 | 1/2013 | Isenhart et al. | |
| 8,478,394 B2 | 7/2013 | Prichep et al. | |
| 8,838,227 B2 | 9/2014 | Causevic et al. | |
| 8,860,570 B2 | 10/2014 | Thomas et al. | |
| 8,948,860 B2 | 2/2015 | Causevic | |
| 2004/0111043 A1 | 6/2004 | Szabo et al. | |
| 2005/0107716 A1* | 5/2005 | Eaton .................. | A61B 5/291 128/903 |
| 2008/0306397 A1 | 12/2008 | Bonmassar et al. | |
| 2009/0312663 A1 | 12/2009 | John et al. | |
| 2010/0198042 A1 | 8/2010 | Popescu et al. | |
| 2011/0099026 A1* | 4/2011 | Oakley ................. | G16H 50/70 705/2 |
| 2012/0124720 A1 | 5/2012 | Evans et al. | |
| 2013/0035579 A1* | 2/2013 | Le .......................... | A61B 5/316 600/383 |
| 2013/0053652 A1* | 2/2013 | Cooner .................. | A61B 5/369 600/595 |
| 2013/0172774 A1 | 7/2013 | Crowder et al. | |
| 2013/0281759 A1* | 10/2013 | Hagedorn ............... | A61N 2/006 600/15 |
| 2013/0338449 A1 | 12/2013 | Warwick et al. | |
| 2014/0163328 A1 | 6/2014 | Geva et al. | |
| 2014/0163408 A1* | 6/2014 | Kocher ................ | A61B 5/7275 600/544 |
| 2014/0333446 A1 | 11/2014 | Newlove | |
| 2015/0005608 A1* | 1/2015 | Evans ....................... | A61B 5/30 600/382 |
| 2015/0038869 A1 | 2/2015 | Simon et al. | |
| 2016/0100794 A1 | 4/2016 | Miller et al. | |

OTHER PUBLICATIONS https://web.archive.org/web/20140207121958/https://www.persyst.com/; Feb. 7, 2014 (Year: 2014).*
Chen et al., "Development of a Portable EEG Monitoring System based on WLAN," IEEE International Conference on Networking, Sensing and Control, pp. 460-465 (2007).
International Search Report dated Aug. 21, 2017 in International Application No. PCT/US2017/036489.
Kim et al., "Helmet-based physiological signal monitoring system," European Journal of Applied Physiology 105:365-372 (2009).
Litscher, "A Multifunctional Helmet for Noninvasive Neuromonitoring," Journal of Neurosurgical Anesthesiology 10(2):116-119 (1998).
Moeller et al., "Quantitative and Qualitative Analysis of Ambulatory Electroencephalography During Mild Traumatic Brain Injury," Archives of Neurology 68(12):1595-1598 (2011).
"New Research to Impact Future of Sports Concussion Diagnosis. Villanova engineering professor's specialized brainwave software has potential to predict and diagnose concussions, PTSD, Alzheimer's disease and sleep disorder," Villanova University Media Room, Jan. 31, 2011 (2 pages).
Nuwer et al., "Routine and quantitative EEG in mild traumatic brain injury," Clinical Neurophysiology 116:2001-2025 (2005).
Oehler et al., "Extraction of SSVEP Signals of a Capacitive EEG Helmet for Human Machine Interface," 30th Annual International IEEE EMBS Conference, pp. 4495-4498 (Aug. 20-24, 2008).
Oh et al., "Wireless Health Monitoring Helmet for Football Players to Diagnose Concussion and Track Fatigue," Nanosensors, Biosensors, and Info-Tech Sensors and Systems 2013, edited by Vijay K. Varadan, Proc. of SPIE vol. 8691, 869106 (7 pages).
Simon et al., "A Portable Non-Invasive Biosensor Based Approach to Actively Assess Sports Concussion and Mild Traumatic Brain Injury (P5.299)," Neurology 82(10 Supplement), Abstract, 6 pages (2014).

* cited by examiner

Top Layer

Bottom Layer

SYSTEMS AND METHODS FOR REAL-TIME CONCUSSION DIAGNOSIS BY ELECTROENCEPHALOGRAM ACTIVITY MONITORING

CROSS-REFERENCE TO RELATED APPLICATIONS

This application is a U.S. National Stage Patent Application under 35 U.S.C. § 371 of International Application No. PCT/US2017/036489, filed on Jun. 8, 2017, which claims priority to U.S. Provisional Application No. 62/347,184 filed Jun. 8, 2016, the contents of each of which are hereby incorporated by reference in their entireties.

BACKGROUND

The disclosed subject matter relates to techniques and systems for real-time diagnosis of head concussions using transmitted electroencephalogram activity monitoring.

Concussion is a form of traumatic brain injury. In the field of sport-related concussion (SRC), certain empiric guidelines for concussion recognition and play removal decisions rely upon subjective player reporting symptoms or an observer raising concern about a high impact injury with potential for concussion. After the concussion occurs, the concussion can be identified based on history and examination, as well as routine neuropsychological tests. Certain laboratory techniques can also identify concussion using quantitative electroencephalogram (qEEG), eye movement abnormalities, high field structural and functional MRI, and elevated levels of certain proteins in the blood.

Certain devices can estimate the impact magnitude of a concussion based on head accelerometry. However, there is variability both within and between patients of concussion risk thresholds, which can prevent such devices from being able to identify concussion. Certain accelerometry and similar warning systems cannot by themself diagnose concussion, but instead, recognize events posing risk for concussion and thus only offer a decision point for further assessment. Further assessments can be time consuming and imprecise, and often rely upon subjective player report to initiate such assessments.

An electroencephalogram (EEG) can be used to monitor brain activity and perform neurological tests in the context of epilepsy diagnosis and management. Although certain EEG monitoring and recording takes place for a brief period in a monitored medical setting using wired connections, ambulatory EEG recording has become used in epilepsy management involving a similar montage for study but with the benefits of portability, and can include a wired montage connected to a small monitoring box. Certain techniques use devices that allow for portable recording as well as real-time monitoring through local broadcasting technologies (e.g., Bluetooth, Wi-Fi, etc.). Although such ambulatory EEG can identify acute transient cortical dysfunctions in a patient experiencing symptomatic concussion in a car accident, patients can experience amnestic symptoms for only 2-3 minutes, which can be too short a time period to diagnose and record such symptoms using conventional techniques. Accordingly, there remains a need to identify concussions in an objective and precise manner. There is also a need to assess real-time changes of measurable physiological brain functions.

SUMMARY

The disclosed subject matter provides systems and methods for real-time concussion diagnosis by electroencephalogram activity monitoring.

In certain embodiments, an exemplary system for detecting concussions in real-time includes an accelerometer to generate an accelerometry signal, a plurality of electrodes to detect an electroencephalogram (EEG) signal from a wearer of a headgear, and a signal processing circuit to amplify, filter and broadcast the EEG signal to a local wireless receiving unit.

In certain embodiments, the plurality of electrodes each can be attached to a top or side region of the headgear through a flexible shaft. Each of the plurality of electrodes can have a leaf spring or a telescoping shaft design. The each of the plurality of electrodes can be in contact with the scalp of the wearer of the headgear and can be connected to the signal processing circuit with a wire. Each of the plurality of electrodes can be at least partially covered with at least one or more of wool felt, conductive rubber, and Ag/AgCl, and each of the plurality of electrodes can be initially wet with saline. Each of the plurality of electrodes can be a conical or a cylindrical shape.

In certain embodiments, the signal processing circuit includes at least one amplifier. The amplifier can be a high impedance input instrumentation amplifier or an operational amplifier. In certain embodiments, signal processing circuit includes a high impedance input instrumentation amplifier and an operational amplifier.

In certain embodiments, the signal processing circuit includes at least one filter. The filter can be a notch filter, a low pass filter, or/and a high pass filter.

In certain embodiments, the signal processing circuit comprises at least one wireless transmitter. The wireless transmitter can be a Bluetooth transmitter or a Wi-Fi transmitter. In certain embodiments, the signal processing circuit comprises a high impedance input instrumentation amplifier; an operational amplifier; a notch filter; a low pass filter; a high pass filter; and at least one wireless transmitter.

In certain embodiments, an exemplary method for detecting concussions in real-time includes measuring an acceleration event, generating an accelerommetry signal, detecting an electroencephalogram (EEG) signal using the plurality of electrodes, amplifying the EEG signal, filtering noise from the EEG signal, and broadcasting the EEG signal to a local wireless receiving unit. The EEG signal can be detected in an earliest period of time after an acceleration event has occurred. The earliest period of time can occur when the accelerommetry signal can fall below a predetermined threshold. In certain embodiments, a quantitative electroencephalography (qEEG) is performed on the EEG signal during relatively quiescent periods. An exemplary method for the qEEG analysis can include calculating a power of the EEG signal in certain frequency components and determining whether a concussion has occurred by comparing the power of the EEG signal to an automated baseline EEG signal acquired from the wearer during periods with no movement. The EEG signal and the qEEG analysis data can be de-identified and encrypted. In certain embodiments, the EEG signal and the qEEG analysis data can be converted to Persyst format.

In certain embodiments, the local wireless receiving unit can analyze the EEG signal through a sideline automated analysis or a cloud based technique. The local wireless receiving unit can record the EEG signal received from the signal processing circuit.

In certain embodiments, the system can have at least one battery wherein the battery is capable to last a typical duration of a sport competition. The system can identify dysfunctional electrodes through automatic intermittent assessments. In certain embodiments, the system can be applicable to other sports headgears including lacrosse helmets, ice hockey helmets, cricket helmets, equestrian helmets, racing helmets, and field hockey helmets, among others, military helmets, construction helmets, mining helmets, and spacesuit helmets.

BRIEF DESCRIPTION OF THE DRAWINGS

Further features and advantages of the present disclosure will become apparent from the following detailed description taken in conjunction with the accompanying figures showing illustrative embodiments of the present disclosure, in which:

FIG. 4a illustrates a top layer layout of the signal processing circuit printed circuit board. FIG. 4b illustrates a bottom layer layout of the signal processing circuit printed circuit board. FIG. 4c illustrates an exemplary circuit diagram of the signal processing circuit.

Figure 1B:
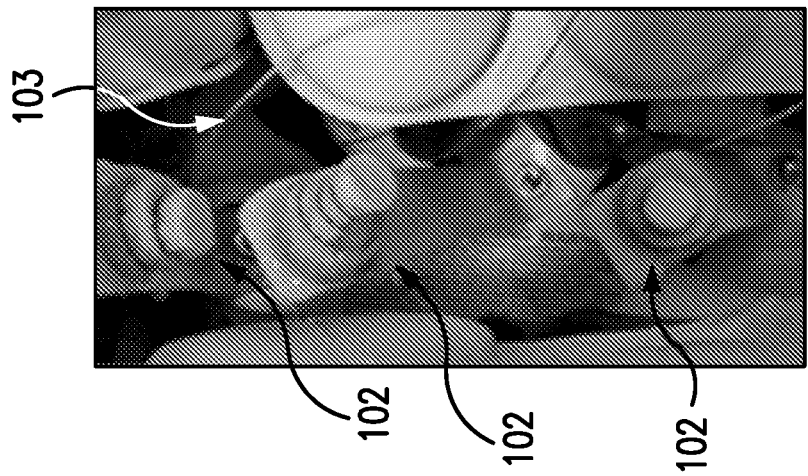
FIGS. 1a and 1b are illustrations of an exemplary system for detecting concussions using an enhanced helmet of the disclosed system in accordance with the present disclosure.

Throughout the figures, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments.

DETAILED DESCRIPTION

Figure 1A:
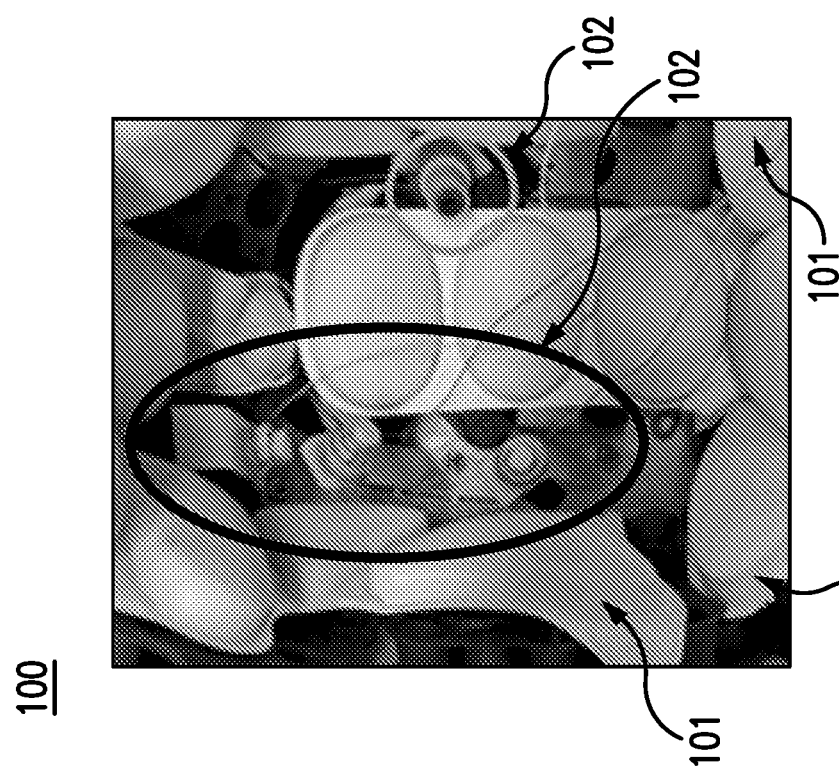

The systems and methods described herein provide for diagnosing concussion in real-time, and as it happens. The systems and methods can perform such a real-time concussion diagnosis without baseline and repeat testing and can identify head injuries resulting from diagnosed concussions. For example, the disclosed subject matter can be integrated into a sports helmet to diagnose concussions suffered by the athlete (e.g., football athlete) wearing the helmet. For the purpose of illustration and not limitation, FIGS. 1a and 1b provide exemplary systems for detecting concussions. In certain embodiments, the disclosed system 100 can include an accelerometry unit (or accelerometer) within the same helmet, which can also broadcast a wireless signal that associates the measured magnitude of impact to a physiological response on an individual basis (e.g., the measured impact magnitude can be normalized based on the physiological response of the individual by comparing against previous impact data). The accelerometer can be coupled to the helmet and can be placed between or beneath pads in the helmet.

With further reference to FIGS. 1a and 1b, the disclosed system 100 can include a plurality of electrodes 102 to detect an electroencephalogram (EEG) signal. For example, and not limitation, EEG signal can be detected by at least one of the plurality of electrodes in an earliest period of time after an acceleration event has occurred. The earliest period of time occurs when the accelerometry signal fall below a predetermined threshold. For example and not limitation, the predetermined threshold can be 5 g after an impact greater than 10 g, at which time the person is most likely uninvolved in significant physical activity which would disturb or degrade the signal by motion artifact. The electrodes can connect to a battery powered signal processing circuit of the disclosed system as described in greater detail below with connection to FIG. 4 through a wire 103.

As shown in FIGS. 1a and 1b, EEG electrodes 102 can be installed within a hard-shell football helmet that meets design specifications to mitigate risk of skull fracture and facial injury. The EEG electrodes 102 can be low profile dry EEG electrodes. The electrodes 102 can provide a connection between the scalp of the wearer of the enhanced helmet and circuitry (e.g., signal processing circuits) of the disclosed system. In some embodiments, additional electrodes that are composed of conductive felt immersed in a conductive saline solution (e.g., athlete's sweat) can be installed within and around the padding within the hard-shell football helmet in an EEG montage (including occipital, parietal, and vertex leads) to assess quantitative EEG. These electrodes can be used to identify EEG signals through scalp and hair. Unlike certain clinical EEG systems, the disclosed system, as shown in FIGS. 1a and 1b, can utilize a reduced montage with three to six electrodes to compute quantitative EEG measures.

As embodied herein, the system 100 can further include a signal processing circuit. For example, the low-profile signal processing circuit can be placed between and/or beneath pads 101 within the helmet to avoid adverse risks of scalp and/or skull injury by its mere placement alone. The signal processing circuit can filter, amplify, and broadcast detected EEG signals to a local wireless network receiver that is able to record and monitor the EEG signals received from the signal processing circuit. In some embodiments, each broadcasting device (e.g., disclosed enhanced helmet) can transmit signals without negatively impacting and/or interfering with signals from other units in order to monitor multiple athletes simultaneously (e.g., a football team during a football game). Additionally, each disclosed system (e.g., disclosed enhanced helmet) can have the battery capacity to last a typical duration of a football or other competition.

Figure 2A:
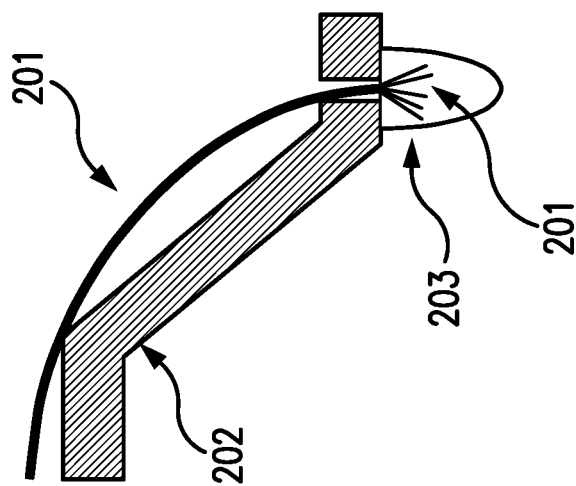
FIGS. 2a, 2b, 2c, and 2d are diagrams illustrating multiple views of each electrode lead used in the disclosed system in accordance with the present disclosure.
Figure 2B:
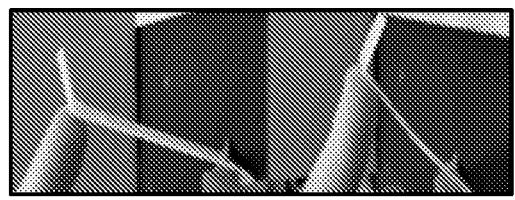
Figure 2D:
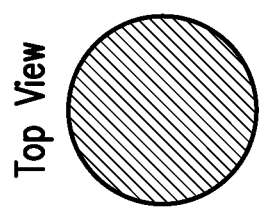
Figure 2C:
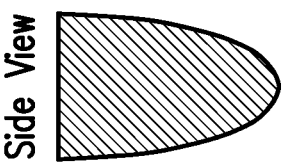

FIGS. 2a, 2b, 2c, and 2d, illustrate multiple views of each electrode lead 200 in the disclosed system. In certain embodiments, the electrode 203 can attach to a top region of the headgear through a flexible shaft 202. As shown in FIG. 2a, the electrode 203 is connected to the system's circuitry through the wire 201. FIG. 2b shows a photograph of the disclosed flexible shaft 202. A side view of the electrode 203 is shown in FIG. 2c. A top view of the electrode 203 is shown in FIG. 2d. An electrode mount, as shown in the example of FIG. 2a, can maintain contact between the electrode 203 and the scalp while being arranged within the helmet in a manner that comfortably fits within the helmet to be worn throughout a game and/or practice. Two electrode mounting systems which are compatible with any electrode design can be designed.

In an embodiment, the electrode mount can be designed in a 'telescoping shaft' type design. For example, FIG. 3a shows a side profile view of the telescoping electrode mount.

Figure 3A:
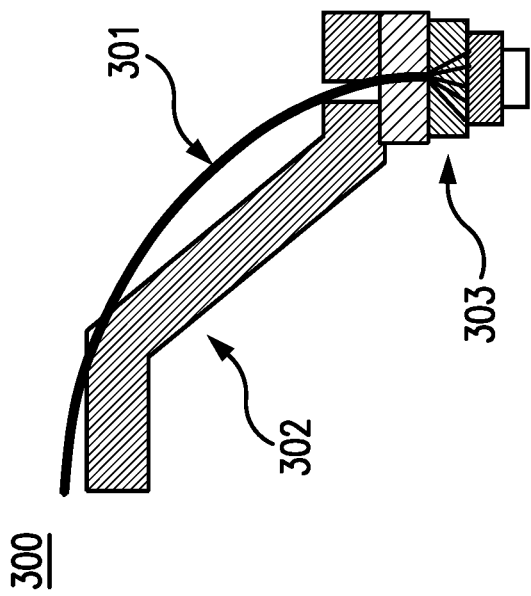
FIGS. 3a, 3b, 3c, 3d, and 3e are diagrams illustrating different views of an example electrode mount in accordance with the present disclosure.
Figure 3E:
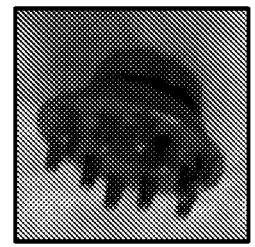
Figure 3D:
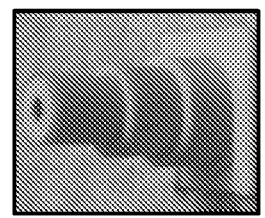
Figure 3C:
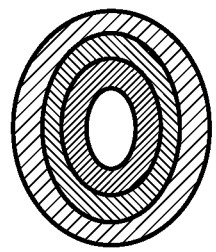
Figure 3B:
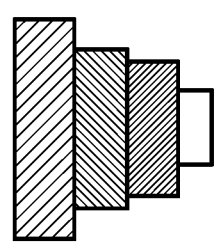

As shown in FIG. 3a, the telescoping shaft type electrode 303 is connected to the system's circuitry through the wire 301. The wire 301 from the amplifier circuit of the system circuitry can be guided by and/or at least partially connected to the flexible shaft 302 and can terminate in the electrode 303 as shown in FIG. 3a. A side view of the electrode 303 is shown in FIG. 3b. A top view of the leaf spring electrode 303 is shown in FIG. 3c.

In another embodiment, the electrode mount can be designed in a 'leaf spring' type design, as those skilled in the art will appreciate. For example, FIG. 3e shows a photograph of the disclosed leaf spring electrode mount 303. The leaf spring electrode mount design can sustain long travel with relatively low force to accommodate different head sizes and shapes. The leaf spring electrode mount design, which can provide a low profile when the electrode mount is compressed, can prevent injury to the scalp during an impact. The leaf spring electrode design can avoid binding and/or lock-up when it is subjected to eccentric loads (e.g., loads subjected to the electrode mount when donning or doffing the helmet and/or loads experienced during an impact, etc). In the telescoping shaft type design, the electrode mount can apply more force than the leaf spring type electrode mount to better maintain contact with the scalp. However, the telescoping shaft type electrode mount cannot withstand as much travel as the leaf spring electrode mount and can be more susceptible to off-axis loads than a leaf spring design.

Figure 4A:
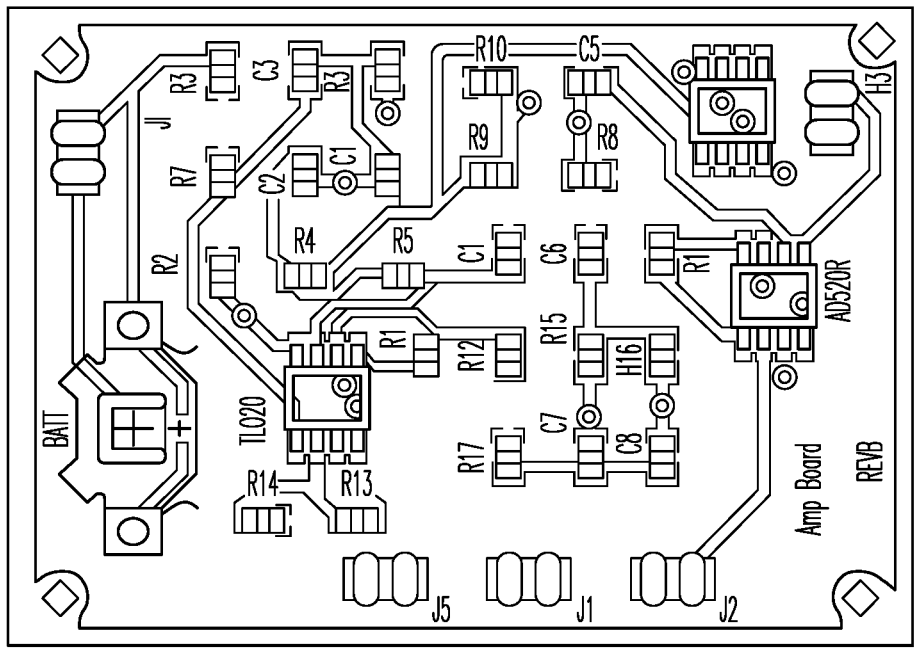
FIGS. 4a, 4b, and 4c illustrate different aspects of example signal processing circuitry of the disclosed system in accordance with the present disclosure.
Figure 4B:
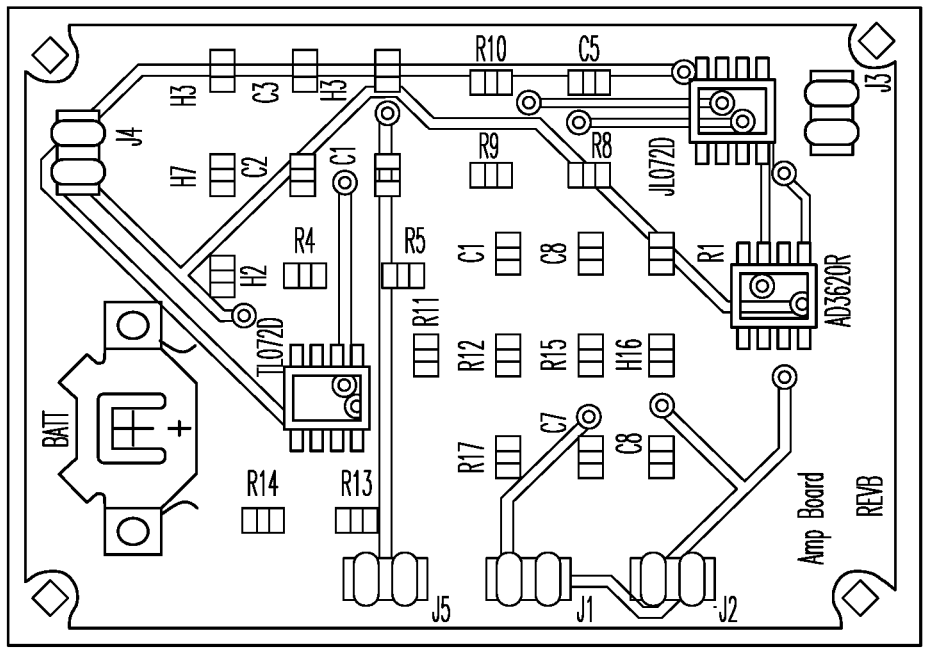
Figure 4C:
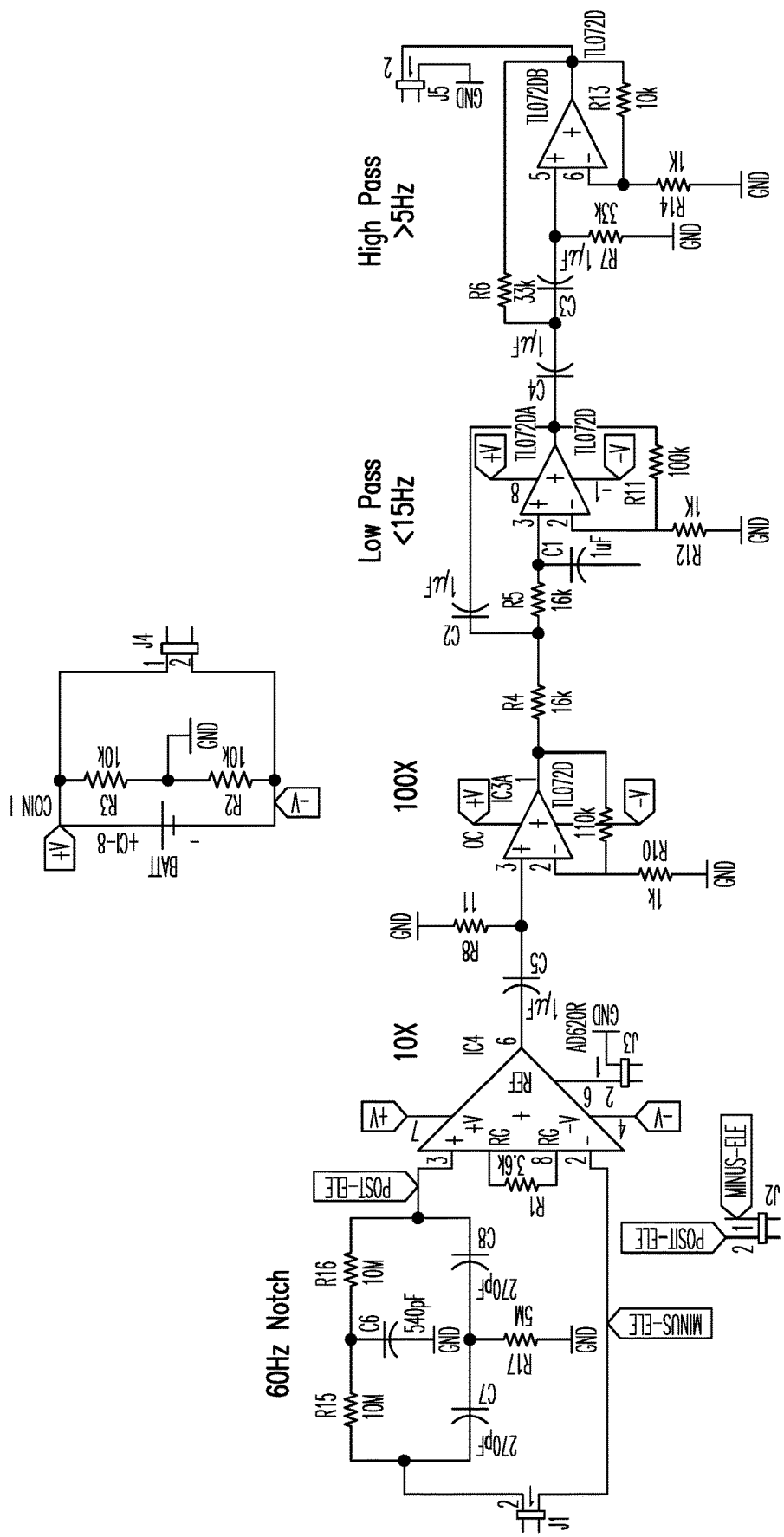

In some embodiments, the electrodes in the helmet can interface between the system's circuitry and the scalp and can reduce the impedance at the scalp-circuitry interface. The electrodes can be designed to be comfortable, non-irritating, and durable. For example, the electrodes for contacting the scalp can be composed of and/or covered at least partially with wool felt, conductive rubber, conductive foam, conductive fabric, and/or sintered Ag/AgCl. When such an enhanced helmet is worn by an athlete during active gameplay, the saline in the sweat produced by the athlete can facilitate conduction between the scalp and the electrodes. Using wool felt allows the electrodes to be comfortable, non-irritating, and durable. The wool felt electrodes can be formed into different shapes with different stiffness levels to penetrate layers of hair. The wool felt electrodes can be conformable to the scalp, resulting in a suitable low impedance interface. The size of the electrodes can be sufficient to reduce the impedance below the mega-Ohm range (e.g., 100 Ohms-10 kOhms based on American Clinical Neurophysiology Society guidelines). In some exemplary implementation, the material used for the electrodes (wool felt, conductive rubber, conductive foam, conductive fabric, Ag/AgCl, etc.) can be designed in conical and/or cylindrical shapes to be able to penetrate through hair and contact the scalp of the wearer. FIGS. 4a, 4b, and 4c illustrate different aspects of the signal processing circuitry of the disclosed system. In some embodiments, EEG potentials recorded on the surface of the scalp can be less than 100 uV, and require an adapted circuit to amplify the meaningful signal while rejecting unwanted noise. Such a circuit, which is illustrated in FIGS. 4a, 4b, and 4c, can be installed in the helmet to reduce coupling of electrical noise in long wires. The signal processing circuit can be arranged into at least two layers of layout. FIG. 4a illustrates a top layer layout of the signal processing circuit printed circuit board. FIG. 4b illustrates a bottom layer layout of the signal processing circuit printed circuit board. FIG. 4c illustrates an exemplary circuit diagram of the signal processing circuit.

As shown in FIG. 4a, the signal processing circuit can include several stages. For example, the signal processing circuit can include a 60 Hz notch filter to remove noise from the alternating current (AC) mains before the signal can be amplified. The signal can be amplified with a high impedance input instrumentation amplifier with a high common mode rejection. The impedance of the instrumentation amplifier can be matched to the impedance of the electrode-scalp interface. The instrumentation amplifier can be followed by and/or connected to an operational amplifier configured to further amplify the signal. Upon amplification by the operational amplifier, the signal can be filtered to remove unwanted frequency components outside the frequencies sensitive to alterations in brain state.

Accordingly, as shown in the exemplary embodiment of FIG. 4c, the operational amplifier can be connected to a low pass filter, which can be connected to a high pass filter. The passband frequencies of the bandpass filter can be more limited than frequencies associated with standard scalp EEG recordings to avoid the high and low frequency ranges that typically contain significant sweat, movement and muscle artifact, while including the frequency bands most likely to be impacted by a diffuse, subtle brain injury. By way of example, and not limitation, the low pass filter can have a cut off frequency of 5-15 Hz and the high pass filter can have a cut off frequency of 0.1-5 Hz. As embodied herein, for example and not limitation, the passband frequencies of the bandpass filter can be in range of 1-40 Hz. The signal can then be wirelessly transmitted to a receiving unit through a transmitter circuit.

In some embodiments, the disclosed system can provide means for addressing impact and minimize movement artifact. For example, the disclosed system can continuously and/or periodically assess the signal to noise ratio (SNR) of the detected EEG signal. Such SNR analyses can cease when the SNR falls below a predetermined threshold (e.g., such as during a substantial impact and/or running). The purpose of such SNR assessment can be to limit battery consumption during low yield recording periods. A hit and/or impact exceeding the acceleration threshold can trigger EEG recording during the earliest quiescent period after the impact. Quiescent periods can be defined as periods in which the accelerometry signal can fall below the predetermined threshold, 5 g after an impact of more than 10 g In this manner, the disclosed system can determine that the enhanced helmet is being worn (e.g., and is not being held in storage) and can activate itself.

The disclosed system can also provide quality assurance. For example, the system can identify any dysfunctional electrodes through intermittent assessments of electrodes. Those electrodes that are not otherwise triggered by the above described mechanism can be identified as dysfunctional and a user can be notified of the problem. Using an accelerometer, the EEG information can be captured after an acceleration event (e.g., potential injury) has occurred, rather than during such an event, to avoid distortions cause by impact.

In some embodiments, the disclosed system can be used to identify neural injury. For example, the disclosed system can automatically assess quantitative electroencephalography (qEEG) during relatively quiescent periods such as between plays (e.g., huddle, while walking/standing in the course of normal play, etc.). qEEG can be a procedure that processes the recorded EEG activity from a multi-electrode recording using processing circuitry.

Figure 5:
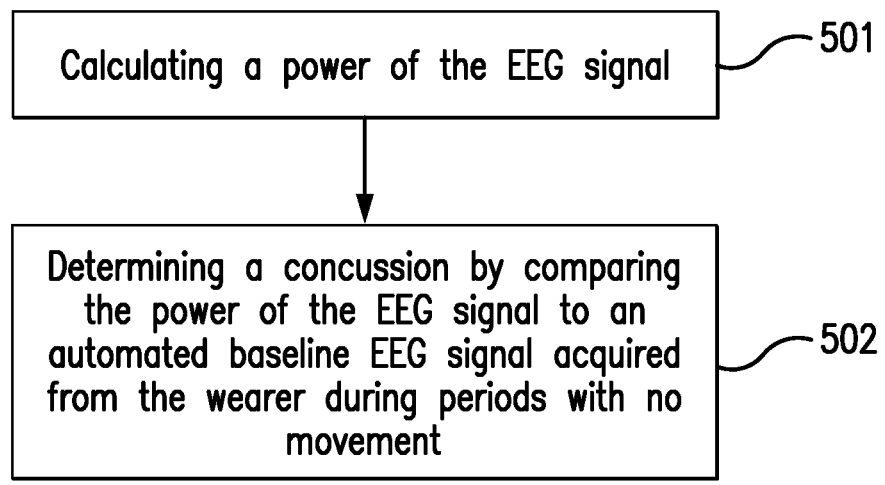
FIG. 5 is a diagram illustrating an exemplary method for quantitative electroencephalography (qEEG) analyses using the system in accordance with the present disclosure.

For the purpose of illustration and not limitation, FIG. 5 provides an exemplary method 500 for qEEG analyses. As illustrated in FIG. 5, the method 500 can include calculating the power of the EEG signal in certain frequency components (e.g. in delta and theta range up to 8 Hz) 501. For example, the EEG signal power can be indicative (e.g., highly sensitive for concussion) and not otherwise identified in normal awake individuals.

Figure 6:
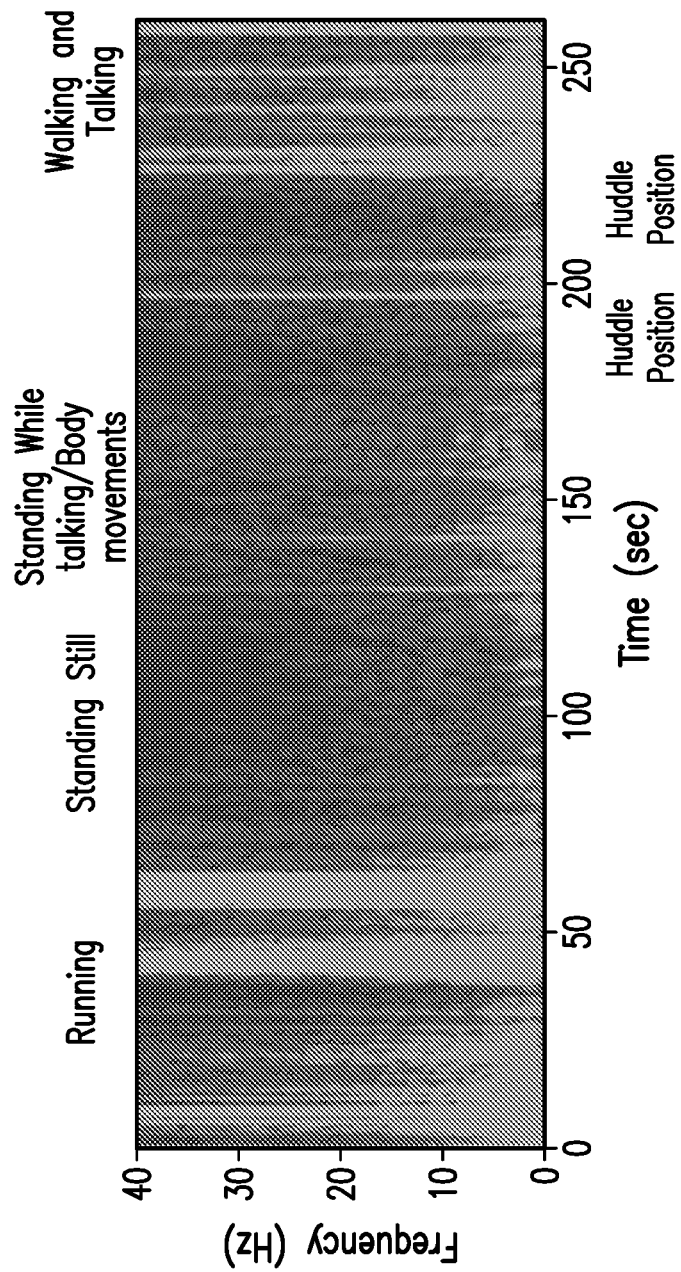
FIG. 6 is a plot illustrating an exemplary spectrogram of a recording from a sweaty athlete.

With further reference to FIG. 5, the method 500 can include determining whether a concussion has occurred by comparing the power of the EEG signal to an automated baseline EEG signal acquired from the wearer during periods with no movement 502. The automated baseline acquisition for comparison during periods with no movement can be repeated periodically during the game. An example of study time can be when the helmet is donned prior to first competitive play of a game. In some embodiments, the disclosed system can monitor and analyze EEG signals while adjusting for resistance as the subject is wearing the helmet and competing in a game. The disclosed system can anticipate a low signal amplitude. For example and not limitation, the low amplitude can indicate a significant change in signal amplitude in the frequency band of interest. The low amplitude signal can have a mean value that is more than two standard deviations less than the mean from the baseline recording, normative dataset, active peers, a significant difference between right and left sides and/or anterior to posterior EEG fields. Additionally and/or alternatively, the disclosed system can anticipate a potentially slowly variable EEG signal measured from a sweating scalp of the subject wearing such an enhanced helmet during competitive play. Given that a fully active player's amount of head sweat does not typically change in short time durations, quantitative EEG cannot be anticipated to be affected by such artifact. For the purpose of illustration and not limitation, FIG. 6 provides an exemplary spectrogram of a wireless recording from an actual sweaty football athlete transmitted to a receiving unit. As shown in FIG. 6, the disclosed system can assess EEG signals of the sweaty athlete between plays such as huddle, running, walking and/or standing still without being affected by the sweat. Each component of the disclosed system can withstand substantial acceleration-deceleration movements including linear, rotational, and translational forces as expected to be encountered in the course of football competition and/or practice.

Figure 7:
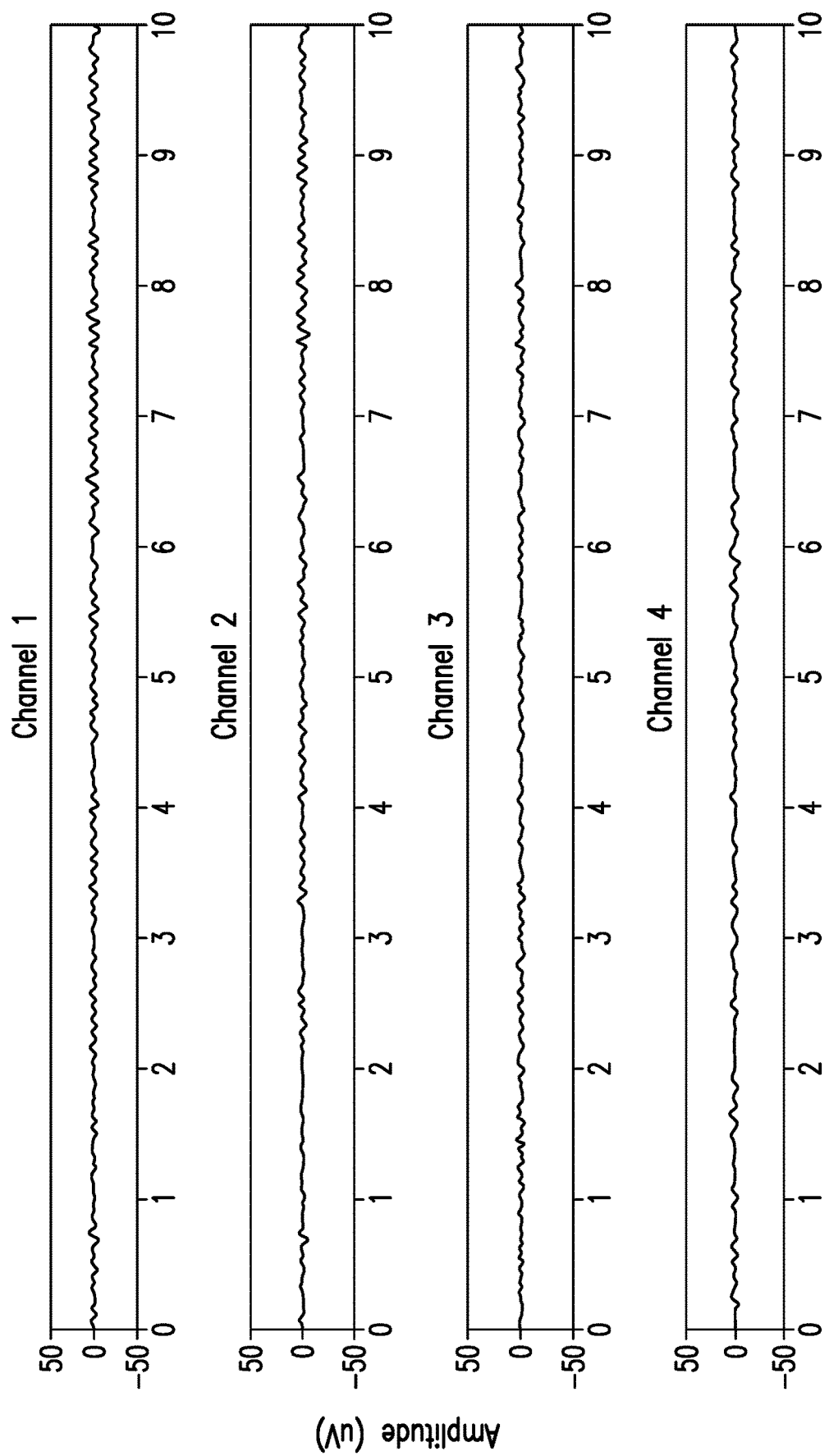
FIG. 7 is a plot illustrating exemplary raw EEG signals
Figure 8:
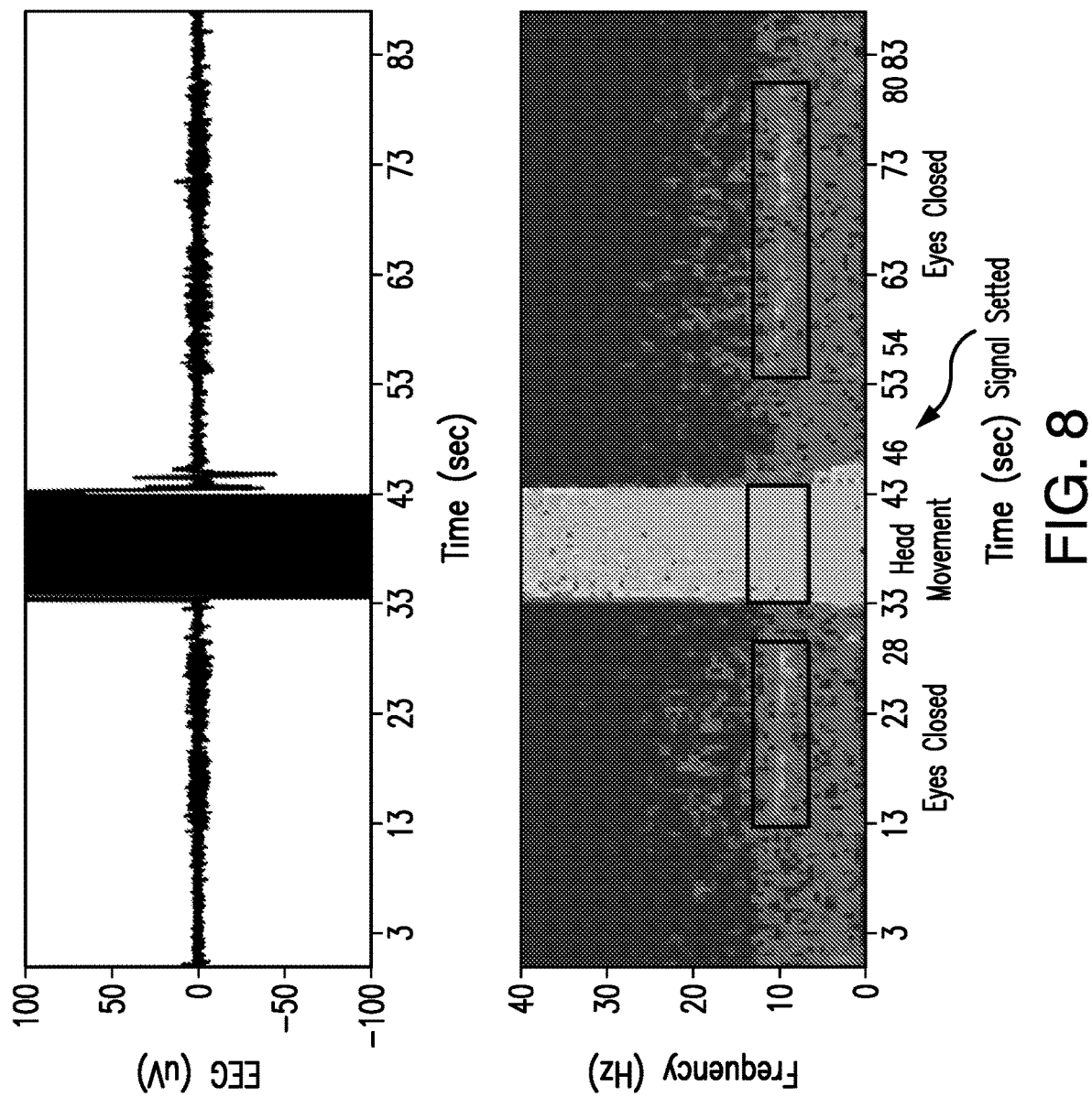
FIG. 8 is a plot illustrating exemplary motion artifacts and recovery of positive EEG signal.

In some embodiments, the presently disclosed system can measure each EEG signal from multiple channels. For the purpose of illustration and not limitation, FIG. 7 provides an exemplary plot of raw EEG signals from four different channels, transmitted wirelessly to a receiving unit. The presently disclosed system can recover EEG signals from motion artifacts. For the purpose of example and not limitation, the spectrogram of FIG. 8 illustrates that artifact EEG signals caused by motions such as head movements can be recovered in 3 seconds in the disclosed system.

In some embodiments, the saline in sweat in the helmet can result in salt-bridging artifacts. A limited montage of electrodes, widely spaced throughout the helmet, along with qEEG analyses, can mitigate negative impacts of salt-bridging artifact(s). An automated algorithm can identify such artifacts due to salt bridges.

The data measured and analyzed by the disclosed system can be transmitted to the receiving unit. Concussion data, which can be triggered by a suspected injury, can be broadcast and/or streamed to the sidelines using wireless technologies maximizing efficiency in power consumption. Such data can be analyzed by sideline automated analyses and cloud based techniques. In resource intense and/or available environments in which large coaching and/or sideline staff is present, sideline automated analyses can be used. In resource poor and/or limited environments such environments with a small coaching and/or sideline staff, cloud-based monitoring can be used in which the helmet data, which can include ongoing live or more in-depth automated monitoring/feedback, can be broadcast.

In some embodiments, the functional ability and broadcast range can be maximized and power consumption can be minimized. For example, the Bluetooth Class 1 transmitters can be used to budget for medium range link (e.g. a range of 100 m which can suffice for anticipated maximum distances from mid-field of 75 m). Triggered and/or intermittent monitoring can be performed as discussed above. Bluetooth 4.0 software, which can eliminate a significant amount of the handshaking associated with other systems (e.g., Wi-Fi), can be used. Other generations of such software with similar or additional functionality can also be employed. Additionally and/or alternatively, the disclosed system can support persistent connections with microwatt-level low power sleep modes to avoid the need for link re-establishment, which typically consumes computation power and radio use time.

In some embodiments, neurological results of multiple athletes can be transmitted to a receiving computer (e.g., tablet, computer, etc. that is used by the coach, medic, etc.). An algorithm can be configured to interpret the data measured by the disclosed system (e.g., enhanced helmet) and classify different neurological states of the subject (e.g., athlete wearing the enhanced helmet) with different colors. For example, normal activity can be indicated by green, questionable injury requiring several seconds of repeat study by yellow, and player out of game and further evaluation triggered and/or required by red. Such a concussion detection algorithm can execute on a mobile application and/or program on the receiving unit's computing circuitry.

In some embodiments, the data measured and/or analyzed by the disclosed system can be saved for subsequent analyses. In some exemplary embodiments, for more detailed EEG examination, the data can be converted to Persyst format and read with Insight and/or other standard EEG "universal translator" review tools. In other embodiments, customized software can be used to process and/or analyze the data measured and/or analyzed by the disclosed system. The data can be stored for analysis of long-term effects of play, repetitive impacts, and baseline changes over longer periods.

In some embodiments, the data measured and analyzed by the disclosed system can be secured. For example, the signal sent from each athlete's enhanced helmet to the receiving unit can be de-identified and encrypted to meet standards related to protected health information. For example, HIPAA safeguards can be implemented for data security of such data and on devices of those analyzing and/or viewing the data.

As described above, the disclosed subject matter can provide the unique advantage of diagnosing transient brain dysfunction pathognomonic symptoms for concussion without having to rely upon athlete reports and/or secondary observation. The disclosed system can allow its users (e.g., coaches, medics, and other health personnel) to quickly and objectively remove an athlete suffering a concussion from the game, regardless of the perceived mechanism and/or magnitude of injury which are not necessarily accurate indicators of the concussion suffered by the athlete. The disclosed system can permit electrodes to contact hair covered portions of the head, rather than the forehead.

Although the disclosed subject matter is discussed within the context of a football helmet in the exemplary embodiments of the present disclosure, the disclosed system can be applicable to any other sports helmets including lacrosse helmets, ice hockey helmets, cricket helmets, equestrian helmets, racing helmets, and field hockey helmets, among others, military helmets, construction helmets, mining helmets, spacesuit helmets, and any other types of helmets. Furthermore, the disclosed system is not limited to helmets and can be applicable to any form of headwear (e.g., caps, head-mounted displays, medical headwear, etc.).

Additionally, while the disclosed subject matter focuses on EEG signal changes associated with transient cortical dysfunction in concussions, a significant proportion of head injuries in football can be associated with fencing tonic response which has been suggested, without physiologic basis, as being non-convulsive activity. However, these movements can be truly convulsive events given their indistinguishable signs relative to fencing posture seizures known to arise from the supplemental motor area and related anterior neocortex. The disclosed systems and methods can diagnose unrecognized seizures in the context of such concussions.

In some embodiments, additionally or alternatively, the presently disclosed system can be integrated into a non-permanent inner padding system of a headgear. For example, a plurality of electrodes with telescoping shaft or leaf spring mounts can be coupled to a pad 101 or an inner bonnet of a headgear to form a wired padding system. The padding system can include the accelerometer to generate an accelerometry signal, a plurality of electrodes to detect EEG signals, and the signal processing circuit to amplify, filter and broadcast the EEG signal to a local wireless receiving unit. In some embodiments, the padding system can be removably attached to a headgear and be interchangeable with a plurality of headgears. The disclosed system can include one or more restraints, straps, buckles, elastic bands, tape, velcro, or any other suitable securing features. For example and not a limitation, the padding system can be coupled to a football helmet through the securing features. The padding system then can be detachable from the football helmet and can be coupled to other headgears. The padding system can be integrated with the disclosed sports helmet comprising additional electrodes.

It will be understood that the foregoing is only illustrative of the principles of the present disclosure, and that various modifications can be made by those skilled in the art without departing from the scope and spirit of the present disclosure.

What is claimed is:

1. A system for detecting concussions suffered by a user in real-time, comprising:
   a protective headgear configured to be worn by the user;
   an accelerometer, adapted to be coupled to the headgear, and configured to measure an acceleration event and generate an accelerometry signal;
   a plurality of electrodes, each adapted for attachment to the headgear; and
   a signal processing circuit, adapted to be coupled to the headgear, and configured to:
      amplify an electroencephalogram (EEG) signal detected by at least one of the plurality of electrodes indicating a concussion suffered by the user;
      filter noise from the EEG signal; and
      broadcast the EEG signal to a local wireless receiving unit, wherein the EEG signal is detected in an earliest period of time after the acceleration event has occurred, wherein the earliest period of time occurs when the accelerometry signal is first able to fall below a predetermined threshold.

2. The system of claim 1, wherein each of the plurality of electrodes is adapted for attachment to the headgear through a flexible shaft.

3. The system of claim 1, wherein each of the plurality of electrodes further comprises at least a partially covering of one or more of wool felt, conductive rubber, conductive foam, conductive fabric, and Ag/AgCl.

4. The system of claim 1, wherein each of the plurality of electrodes comprises a conical or a cylindrical shape.

5. The system of claim 1, wherein each of the plurality of electrodes is selected from the group consisting of a leaf spring electrode and a telescoping shaft electrode.

6. The system of claim 1, wherein the signal processing circuit comprises at least one amplifier selected from the group consisting of a high impedance input instrumentation amplifier and an operational amplifier.

7. The system of claim 1, wherein the signal processing circuit comprises at least one filter selected from the group consisting of a notch filter, a low pass filter, and a high pass filter.

8. The system of claim 1, wherein the signal processing circuit comprises at least one wireless transmitter selected from the group consisting of a Bluetooth transmitter and a Wi-Fi transmitter.

9. The system of claim 1, wherein the signal processing circuit comprises a high impedance input instrumentation amplifier; an operational amplifier; a notch filter; a low pass filter; a high pass filter; and at least one wireless transmitter.

10. A method for detecting concussions in real-time using a detection system, coupled to a pad, including an accelerometer and a plurality of electrodes, comprising:
    measuring an acceleration event using the accelerometer;
    generating an accelerometry signal;
    detecting an electroencephalogram (EEG) signal using the plurality of electrodes;
    amplifying the EEG signal in the detection system;
    filtering noise from the EEG signal; and
    broadcasting the EEG signal to a local wireless receiving unit, wherein the EEG signal is detected in an earliest period of time after the acceleration event has occurred, wherein the earliest period of time occurs when the accelerometry signal is first able to fall below a predetermined threshold.

11. The method of claim 10, wherein a quantitative electroencephalography (qEEG) is performed on the EEG signal during relatively quiescent periods, including:
    calculating a power of the EEG signal in frequency components; and
    determining whether the concussion has occurred by comparing the power of the EEG signal to an automated baseline EEG signal acquired from a user during periods with no movement.

12. The method of claim 11, wherein the EEG signal and the qEEG analysis data are de-identified and encrypted.

13. The method of claim 11, wherein the EEG signal and the qEEG analysis data are converted to Persyst format.

14. The method of claim 10, wherein the broadcasting comprises analyzing the EEG signal through a sideline automated analysis or a cloud based technique.

15. The method of claim 10, further comprising recording the EEG signal.

16. A padding system for detecting concussions in real-time, comprising:

an accelerometer, coupled to a pad, and configured to measure an acceleration event and generate an accelerometry signal;

a plurality of electrodes, each of the plurality of electrodes are coupled to the pad; and a signal processing circuit, coupled to the pad, and configured to:

amplify an electroencephalogram (EEG) signal detected by at least one of the plurality of electrodes indicating a concussion suffered by a user;

filter noise from the EEG signal; and broadcast the EEG signal to a local wireless receiving unit, wherein the EEG signal is detected in an earliest period of time after the acceleration event has occurred, wherein the earliest period of time occurs when the accelerometry signal is first able to fall below a predetermined threshold.

17. The padding system of claim 16, wherein the padding system is removably attached to a headgear.

18. The padding system of claim 16, wherein each of the plurality of electrodes further comprises at least a partially covering of one or more of wool felt, conductive rubber, conductive foam, conductive fabric, and Ag/AgCl.

19. The padding system of claim 16, wherein each of the plurality of electrodes comprises a conical or a cylindrical shape.

20. The padding system of claim 16, wherein each of the plurality of electrodes is selected from the group consisting of a leaf spring electrode and a telescoping shaft electrode.

21. The padding system of claim 16, wherein the signal processing circuit comprises at least one amplifier selected from the group consisting of a high impedance input instrumentation amplifier, and an operational amplifier.

22. The padding system of claim 16, wherein the signal processing circuit comprises at least one filter selected from the group consisting of a notch filter, a low pass filter, and a high pass filter.

23. The padding system of claim 16, wherein the signal processing circuit comprises at least one wireless transmitter selected from the group consisting a Bluetooth transmitter, a Wi-Fi transmitter, and combinations thereof.

24. The padding system of claim 16, wherein the signal processing circuit comprises a high impedance input instrumentation amplifier; an operational amplifier; a notch filter; a low pass filter; a high pass filter; and at least one wireless transmitter.

* * * * *